US006153202A

United States Patent [19]

Klesius et al.

[11] Patent Number: 6,153,202

[45] Date of Patent: Nov. 28, 2000

[54] IN OVO METHODS FOR UTILIZING LIVE *EDWARDSIELLA ICTALURI* AGAINST ENTERIC SEPTICEMIA IN CHANNEL CATFISH

[75] Inventors: Phillip H. Klesius, Auburn; Craig A. Shoemaker, Notasulga, both of Ala.; Joyce J. Evans, Chestertown, Md.

[73] Assignee: The United States of America as represented by the Secretary of Agriculture, Washington, D.C.

[21] Appl. No.: 09/369,563

[22] Filed: Aug. 6, 1999

Related U.S. Application Data

[63] Continuation-in-part of application No. 09/053,261, Mar. 6, 1998, Pat. No. 6,019,981.

[51] Int. Cl.$^7$ .......................... A61K 39/02; A61K 39/00; A61K 39/116; A01N 63/00

[52] U.S. Cl. .................. 424/234.1; 424/93.2; 424/93.48; 424/93.4; 424/200.1; 424/203.1; 424/184.1; 424/93.1; 424/827

[58] Field of Search ............................. 424/200.1, 234.1, 424/827, 9.2, 93.2, 93.4, 93.48, 172.1, 184.1, 235.1, 203.1

[56] References Cited

U.S. PATENT DOCUMENTS

| | | | |
|---|---|---|---|
| 5,151,023 | 9/1992 | Kuzuhara et al. | 424/89 |
| 5,284,653 | 2/1994 | Wolf-Eatz et al. | 424/92 |
| 5,747,309 | 5/1998 | Allan et al. | 435/172.3 |
| 5,780,448 | 7/1998 | Davis | 514/44 |
| 6,010,705 | 1/2000 | Thune et al. | 424/234.1 |
| 6,019,981 | 2/2000 | Klesius et al. | 424/234.1 |

OTHER PUBLICATIONS

Plumb et al. J. Fish Dis. 11: 499–509, 1988.

Klesius et al. Adv. Vet. Med. 41: 523–537, abstract, 1999.

Thune et al. Dev. Biol. Stand. 90: 125–134, 1997.

Goudie et al. In: Proc. Inter. Fish Physiol. Symp., University of British Columbia, Vancouver, Canada, Jul. 16–21, pp. 150–155, 1994.

Awad et al. J. Aquat. Anim. Sci. 1: 233–237, 1989.

*Primary Examiner*—James C. Housel
*Assistant Examiner*—S. Devi
*Attorney, Agent, or Firm*—M. Howard Silverstein; Joseph A. Lipovsky; John D. Fado

[57] ABSTRACT

Methods for the safe and effective live in ovo vaccination of eyed eggs of catfish against enteric septicemia of catfish (ESC) were created through the use of rifampicin resistant native E. ictaluri isolates; these including rifampicin-resistant strain ATCC 202058 of *Edwardsiella ictaluri* originally isolated from the walking catfish Clarius batrachus from Thailand. Single immersion exposure of eyed eggs of catfish stimulated strong acquired immunity against many isolates of E. ictaluri without the need for booster immunization.

6 Claims, No Drawings

IN OVO METHODS FOR UTILIZING LIVE *EDWARDSIELLA ICTALURI* AGAINST ENTERIC SEPTICEMIA IN CHANNEL CATFISH

This case is a continuation-in-part of U.S. application Ser. No. 09/053,261 filed Mar. 6, 1998, now U.S. Pat. No. 6,019,981.

BACKGROUND OF THE INVENTION

1. Field of the Invention

*Edwardsiella ictaluri,* the causative agent of enteric septicemia of catfish (ESC) is a Gram-negative bacterium that is highly infectious for the channel catfish *Ictalurus punctatus.* This pathogen has been isolated from channel catfish in most areas of the United States where this species is cultured and from walking catfish in Thailand [Kasornchandra et al., *J. Fish Dis.* 10:137–138(1987). Losses in fingerlings to market-size fish account for about 50% of the total disease losses to catfish producers. Formalin-killed bacterial vaccines have not been successful due to their provoking only a humoral response. This is due to *Edwardsiella ictaluri* being an intracellular pathogen, with acquired immunity in fish surviving ESC being more cellular than humoral.

This invention relates to novel vaccine methods against ESC which provides effective in ovo protection; this being related to its ability to stimulate cellular-immunity and protection.

2. Description of the Prior Art

It has been estimated that ESC is responsible for annual losses of 20 to 30 million dollars in the catfish industry. Control of *E. ictaluri* has been attempted by feeding antibiotic medicated feed. This expensive practice has been ineffective because sick fish do not eat and antibiotic resistance to oxytetracycline and ormethoprim-sulfamethoxine, the approved drugs for use on food fish, has been observed.

Based on the success of disease control by bacterin immunization of salmonids, bacterins were developed against ESC. An *E. ictaluri* bacterin (ESC vaccine, ALPHARMA, formerly BIOMED, Inc., 1720-130th Ave. N.W., Bellevue, Wash., USA) was produced and marketed with a provisional license for immersion vaccination of channel catfish against ESC. An oral *E. ictaluri* bacterin (Escogen, Aqua Health, Ltd., Charlottetown, PEI, Canada) was produced, marketed and licensed for oral vaccination of channel catfish against ESC. Thune et al. [*J. Appl. Aquaculture* 3, 11–23 (1994)] teach that vaccination of channel catfish (*Ictalurus punctatus*) with *E. ictaluri* bacterins has not resulted in acquired immunity of long duration. Nusbaum and Morrison [*J. Aquat. Animal Health* 8, 146–149 (1996)] also demonstrated that killed *E. ictaluri* was not entering the fish and suggested that this affected vaccine efficacy. *Edwardsiella ictaluri* has been described as a facultative intracellular pathogen of channel catfish [Miyazaki et al.; *J. Fish Dis.* 8, 389–392 (1985)]. Because of the nature of *E. ictaluri* as an intracellular pathogen, it is not surprising that killed vaccines have not been successful. Strictly controlled live vaccination of channel catfish with low concentrations of unmodified isolates of *E. ictaluri* by bath immersion was found to stimulate protective immunity, specific antibodies by Klesius et al. [Journal of Aquatic Animal Health 7, 205–210 (1995)]. Protective immunity to *B. abortus* in cattle was demonstrated by Montaraz et al. [*Infect. Immun.* 53, 245–251 (1986)] and Schurig et al. [*Vet. Micro.* 28, 171–188 (1991)] using vaccines based on modified live rifampicin-resistant Brucella species.

SUMMARY OF THE INVENTION

We have now discovered in ovo methods that are safe and effective for the control of ESC in catfish. The vaccines comprise one or more rifampicin (3-[4-methylpiperazinyl-iminomethyl]rifamycin SV) (Sigma Chemical Company, St. Louis, Mo.) resistant mutant isolates of *E. ictaluri,* created by multiple passaging of native isolates on increasing concentrations of rifampicin. These vaccines are effective in providing long lasting acquired immunity in channel catfish to ESC.

In accordance with this discovery, it is an object of the invention to provide in ovo live vaccination against ESC in catfish.

It is also an object of this invention to provide for in ovo vaccination of catfish utilizing both monovalent and polyvalent vaccines against ESC.

It is a further object of this invention to improve the viability and productivity of catfish, and to reduce economic losses in the catfish industry caused by ESC.

Other objects and advantages of the invention will become readily apparent from the ensuing description.

DEPOSIT OF BIOLOGICAL MATERIAL

Rifampicin-resistant attenuated *Edwardsiella ictaluri* isolate EILO RE-33, was deposited on Nov. 26, 1997, under the provisions of the Budapest Treaty with the American Type Culture Collection located at 10801 University Boulevard, Manassas, Va. 20110-2209, and has been assigned Accession No. ATCC 202058.

Rifampicin-resistant attenuated *Edwardsiella ictaluri* isolates RA-75-34, RS-629-34, and RS-694-34 were deposited on Jan. 12, 1998 under the provisions of the Budapest Treaty in the Agricultural Research Service Culture Collection located at 1815 North University Street, Peoria, Ill. 61604, and have been assigned Deposit No.'s B-21909, B-21910, and B-21911 respectively.

DETAILED DESCRIPTION OF THE INVENTION

"Vaccine" is defined herein in its broad sense to refer to any type of biological agent in an administratable form capable of stimulating a protective immune response in an animal inoculated with the vaccine. For purposes of this invention, the vaccine may comprise one or more live attenuated isolates of *Edwardsiella ictaluri* having the characteristic of rifampicin-resistance.

The starting material for use in preparing the vaccines of the invention may be any isolate of *Edwardsiella ictaluri.* Serial passage of the isolate of *Edwardsiella ictaluri* over increasing concentrations of rifampicin produces strains with an attenuated pathogenicity efficacious for the preparation of live vaccines. The methodology for attenuation by serial passage is well known and documented in the art as exemplified by Schurig et al. [*Vet. Micro.* 28, 171–188 (1991)], hereby incorporated by reference, who created vaccines based on modified live rifampicin-resistant Brucella species.

The term "revertant" is intended to refer to a subculture of an attenuated bacterium, the subculture being characterized by increased virulence and increased in vivo replication as compared to the attenuated form. The term is used herein generically to encompass both true revertants and apparent revertants, the latter being derived from an existing bacterial population.

The term "in ovo" is intended to refer to the treatment of eyed eggs of catfish prior to hatch.

The term "eyed egg" refers to that stage in egg development where the eye of the fish embryo is visible through the egg wall. This typically occurs in catfish 4–5 days after egg laying, and 3–4 days prior to hatch, where the water temperature is 78° F.

The starting material for use in preparing the vaccines of the invention is any attenuated *Edwardsiella ictaluri* bacterium such as the ATCC 202058 bacterium reported supra. The attenuation achieved by high-level serial passage in culture on increasing concentrations of rifampicin virtually eliminates the pathogenicity of the bacterium toward channel catfish. The native strain of *Edwardsiella ictaluri* should be passaged a sufficient number of times such that in its new attenuated form it no longer possesses the ability of causing the disease state known as enteric septicemia in catfish. The efficacy of the monovalent vaccine against challenge by certain strains of native *Edwardsiella ictaluri* is however not universal. The vaccinal efficacy can be enhanced by combining multiple attenuated strains of *Edwardsiella ictaluri* into bivalent or polyvalent vaccines.

Vaccination, while being accomplishable by injection or through oral ingestion, is most efficiently done by means of aqueous immersion. The bacterial agent is prepared for administration by formulation in an effective immunization dosage with an acceptable carrier or diluent, such as water. The expression "effective immunization dosage" is defined as being that amount which will induce immunity in a catfish against challenge by a virulent strain of ESC. Immunity is considered as having been induced in a population of catfish when the level of protection for the population is significantly higher than that of an unvaccinated control group. Typically, vaccination is carried out by exposing channel catfish eyed eggs by immersion in water containing about $1\times10^5$ CFU/ml of attenuated *Edwardsiella ictaluri* for ten minutes at a density of about 50 grams of eyed fish eggs per liter of water and vaccine and a temperature of about 25° C. These parameters may be varied as desired such that a sufficient level of vaccination is acquired without induction of excessive loss. Useable concentrations of *Edwardsiella ictaluri* are considered to range from about $5\times10^4$ to about $1\times10^8$ CFU/ml of immersion medium. Useable vaccination times are seen to range from about 2 minutes to about 60 minutes, preferably from about 2 minutes to about 10 minutes. Temperature of the inoculation media may range within the physiologically acceptable limits of catfish, preferably from about 20° C. to about 28° C., most preferably from about 22° C. to about 26° C. Concentrations of eyed fish eggs treated in the inoculation medium typically range from about 50 grams to about 100 grams per liter of immersive innoculant.

Appropriate adjuvants as known in the art may also be included in the vaccine formulation. In many cases, the vaccinal efficacy can be enhanced by combining the different strains of attenuated *Edwardsiella ictaluri* into bivalent or polyvalent vaccines.

The following examples are intended only to further illustrate the invention and are not intended to limit the scope of the invention which is defined by the claims.

EXAMPLE 1

The procedure used to produce the ATCC 202058 vaccine was modified from that described in Shurig et al. (1991; Vet Micro 28, 171–188), hereby incorporated by reference, by using a lower initial concentration of rifampicin and ending at 320 μg/ml instead of 200 μg/ml and by omitting the penicillin step.

Process of Developing Resistant Mutants of *Edwardsiella ictaluri*

Brain heart infusion agar plates for the cultivation of *Edwardsiella ictaluri* were made according to the procedure of Difco (Difco, Inc., Detroit, Mich.). 37 g of brain heart infusion media and 17 g of agar are added to one liter of distilled water. The media and agar were heated until dissolution. The media was then autoclaved at 121–124° C. for 15 minutes, the media was then poured into sterile petri dishes (15 ml per dish) and allowed to solidify before refrigeration.

Native isolates of *Edwardsiella ictaluri* were obtained from sick catfish or previously obtained lyophilized stocks. Isolates of *E. ictaluri* were then identified by standard biochemical tests as set forth in *Bergey's Manual of Determinative Bacteriology* prior to use in rifampicin resistant *E. ictaluri*. After identification, the process of forming rifampicin resistant isolates of *Edwardsiella ictaluri* was begun. Rifampicin supplemented brain heart infusion agar plates were prepared as follows: Brain heart infusion agar was made as described above and sterilized at 121–124° C. for 15 minutes. After sterilization, the correct amount of rifampicin was added to the media prior to its solidification and 15 ml of the resulting mixture was poured into separate petri dishes and allowed to solidify prior to refrigerated storage. Initial cultures of the native isolates of *Edwardsiella ictaluri* were grown on brain heart infusion agar plates which were incubated at 20–25° C. for 24–48 hours or until 1–2 mm translucent colonies were observed. A single *E. ictaluri* colony was then picked with a sterile inoculating loop and streaked onto a rifampicin supplemented brain heart infusion agar plate containing the correct concentration of the antibiotic. For the initial passage, rifampicin was present in the brain heart infusion agar at a concentration of 5 μg/ml. The rifampicin supplemented brain heart infusion agar which was streaked with the aforementioned native isolate of *E. ictaluri* was then incubated for 24–48 hours at 20–25° C. and observed for bacterial growth. Single colonies of *E. ictaluri* which grew on the rifampicin supplemented media were then picked and placed onto the next concentration of rifampicin (10 μg/ml) brain heart infusion agar plates. If growth occurs, a single colony is harvested and placed on an agar media containing the next higher concentration of rifampicin (20 μg/ml). If the harvested colony failed to grow, it was repeatedly passed on a media containing the last concentration of rifampicin at which growth successfully occurred, before being placed on the next higher concentration of rifampicin containing media. This process was repeated until a colony capable of growing on a media containing a rifampicin concentration of 320 μg/ml was created.

*Edwardsiella ictaluri* isolate ATCC 202058 was passaged on increasing concentrations of rifampicin (3-[4-methylpiperazinyl-iminomethyl]rifamycin SV) (Sigma Chemical Company, St. Louis, Mo.) supplemented brain heart infusion (BHI) agar to a final concentration of 320 μg/ml rifampicin for 33 passages. The resultant mutant, designated ATCC 202058, is differentiated from the parent microorganism because it can survive and reproduce without negative effect on a media containing 320 μg/ml rifampicin. Biochemical characteristics of the *E. ictaluri* ATCC 202058 are identical to *E. ictaluri* as described in *Bergey's Manual of Determinative Bacteriology* (Holt et al.,1994), herein incorporated by reference.

EXAMPLE 2

Eyed channel catfish eggs totaling 500 grams in weight were vaccinated by immersion with about $1\times10^5$ CFU/ml ATCC 202058 vaccine for ten minutes at a density of about 50 grams of eyed eggs/L in 24–26° C. water. The fish subsequently hatched from the immunized eggs were kept in 1500L fiberglass tanks supplied with recirculating well water at 26° C. with a flow rate of 0.5L/minute. Fish were fed daily a commercial catfish ration amounting to 4% of their body weight. Fish utilized in the experiment ranged in size from about 3 grams to about 5 grams and ranged from about 33 to about 36 days of age. Fish were observed daily for mortalities, abnormal behavior, and to monitor for any signs of ESC. In the experiment, consisting of a trial lasting from 33 to 36 days post vaccination, no signs of ESC or mortality were seen in any of the fish. The results are presented below in Table I.

TABLE I

PROTECTION AGAINST ENTERIC SEPTICEMIA OF CATFISH (ESC) AFTER IMMERSION VACCINATION OF EYED CHANNEL CATFISH EGGS WITH *EDWARDSIELLA ICTALURI* VACCINE (ATCC 202058)

| | # Dead fish/ # challenged | % mortality | Relative percent survival (RPS) |
|---|---|---|---|
| Control[a] | | | |
| Tank 1 | 24/30 | 80.0 | |
| Tank 2 | 6/30 | 20.0 | |
| Tank 3 | 11/30 | 36.6 | |
| | | mean 45.5 | |
| Vaccinated | | | |
| Tank 1 | 5/30 | 16.6 | |
| Tank 2 | 0/30 | 0.0 | |
| Tank 3 | 0/30 | 0.0 | |
| | | mean 5.5 | 87.9 |

[a]non-vaccinated eggs

Eyed egg mass (500 g) vaccinated with ATCC 202058 modified live *E. ictaluri* vaccine in 9.5 liters of water; 33 to 36 day old fish were challenged with *E. ictaluri* (AL-93-75) by immersion. Eggs were vaccinated in water and vaccine for 10 minutes. No fish died after vaccination.

Results of experimental challenge are presented as relative percent survival (RPS) as described by Amend (1981; Dev. Biol. Stand. 49, 447–454),herein incorporated by reference. RPS is calculated according to the following formula:

$$RPS = 1 - \frac{\%\ \text{vaccinate mortality}}{\%\ \text{control mortality}} \times 100$$

At sixteen days post challenge (DPC) the relative percent survival was 87.9%. Five of 90 vaccinates died after challenge. In this study, mortality in an equivalent group of 90 untreated controls was 41 of 90 or 45.5%.

It is understood that the foregoing detailed description is given merely by way of illustration and that modification and variations may be made therein without departing from the spirit and scope of the invention.

We claim:

1. A method comprising administering a composition to eyed eggs of catfish one or more attenuated mutant strains of *Edwardsiella ictaluri* resistant to rifampicin and effective in eliciting an immune response in catfish which is protective against infection by virulent strains of *Edwardsiella ictaluri.*

2. The method of claim 1 wherein said administration is by means of immersion in an aqueous system.

3. The method of claim 2 wherein said attenuated strain of *Edwardsiella ictaluri* is present in the immersion bath at a concentration greater than or equal to about $1\times10^5$/ml.

4. The method of claim 1 wherein two or more strains of *Edwardsiella ictaluri* are utilized to provide protection for catfish against infection by virulent strains of *Edwardsiella ictaluri.*

5. The method of claim 4 wherein said administration is by means of immersion in an aqueous system.

6. The method of claim 5 wherein each of said attenuated strains of *Edwardsiella ictaluri* are present in the immersion bath at a concentration greater than or equal to about $1\times10^5$/ml.

* * * * *